US011089966B2

(12) United States Patent
Zhao et al.

(10) Patent No.: US 11,089,966 B2
(45) Date of Patent: Aug. 17, 2021

(54) DEVICES AND METHODS FOR NON-INVASIVE CAPILLARY BLOOD PRESSURE MEASUREMENT

(71) Applicants: The Chinese University of Hong Kong, Hong Kong (CN); Massachusetts Institute of Technology, Cambridge, MA (US)

(72) Inventors: Ni Zhao, Guangdong (CN); Jing Liu, Hubei (CN); Charles Sodini, Belmont, MA (US)

(73) Assignees: The Chinese University of Hong Kong, Hong Kong (CN); Massachusetts Institute of Technology, Cambridge, MA (US)

( * ) Notice: Subject to any disclaimer, the term of this patent is extended or adjusted under 35 U.S.C. 154(b) by 504 days.

(21) Appl. No.: 15/972,653

(22) Filed: May 7, 2018

(65) Prior Publication Data
US 2019/0336016 A1    Nov. 7, 2019

(51) Int. Cl.
*A61B 5/021*    (2006.01)
*A61B 5/0295*    (2006.01)
(Continued)

(52) U.S. Cl.
CPC ........ *A61B 5/02108* (2013.01); *A61B 5/0261* (2013.01); *A61B 5/0295* (2013.01);
(Continued)

(58) Field of Classification Search
CPC ............ A61B 5/02108; A61B 5/02116; A61B 5/02225; A61B 5/02241; A61B 5/02255; A61B 5/0261; A61B 5/0295; A61B 5/6816; A61B 5/6824; A61B 5/6826; A61B 5/6828; A61B 5/6829; A61B 5/6843; A61B 5/7203; A61B 8/02; A61B 8/04; A61B 8/06; A61B 8/0891; A61B 8/403;
(Continued)

(56) References Cited

U.S. PATENT DOCUMENTS 6,217,524 B1    4/2001 Orr et al.
2011/0144514 A1*   6/2011 Booker ............. A61M 16/0475
                                                    600/529

(Continued)

FOREIGN PATENT DOCUMENTS

WO    WO-02/094094 A1    11/2002

*Primary Examiner* — Michael T Rozanski
(74) *Attorney, Agent, or Firm* — Saliwanchik, Lloyd & Eisenschenk

(57) ABSTRACT

Devices and methods for non-invasive capillary blood pressure measurement are provided. An device can comprise a front end in contact with the body to compress and decompress the capillaries in the tissue, a pressure control module for regulating the contact pressure between the front end and the tissue, a pressure transducer coupled to the front end for measuring the contact pressure, a capillary sensing module for detecting the capillaries pulsations under the contact pressure modulation, and an algorithm for determining the capillaries pressures from the traces of capillary pulsation signals and the contact pressure signal. The methods include an oscillometric method for intermittent arterial and capillary blood pressure measurement and a volume-clamp method for continuous capillary blood pressure measurement.

18 Claims, 6 Drawing Sheets

(51) Int. Cl.
*A61B 5/022* (2006.01)
*A61B 8/04* (2006.01)
*A61B 5/00* (2006.01)
*A61B 5/026* (2006.01)
*A61B 8/02* (2006.01)
*A61B 8/06* (2006.01)

(52) U.S. Cl.
CPC ...... *A61B 5/02225* (2013.01); *A61B 5/02241* (2013.01); *A61B 5/6824* (2013.01); *A61B 5/6826* (2013.01); *A61B 5/6828* (2013.01); *A61B 5/6829* (2013.01); *A61B 5/6843* (2013.01); *A61B 5/7203* (2013.01); *A61B 8/02* (2013.01); *A61B 8/04* (2013.01); *A61B 8/06* (2013.01)

(58) Field of Classification Search
CPC ... A61B 8/4209; A61B 8/4227; A61B 8/5223; G16H 50/30
See application file for complete search history.

(56) References Cited

U.S. PATENT DOCUMENTS

| | | | |
|---|---|---|---|
| 2011/0197888 A1* | 8/2011 | Deutsch ............ | A61M 16/0479 128/204.23 |
| 2014/0076309 A1* | 3/2014 | Takeda .................... | A61F 7/123 128/200.26 |
| 2017/0231562 A1* | 8/2017 | Park ....................... | A61B 5/021 600/485 |

* cited by examiner

DEVICES AND METHODS FOR NON-INVASIVE CAPILLARY BLOOD PRESSURE MEASUREMENT

FIELD OF THE INVENTION

This invention relates to devices and methods for non-invasive capillary blood pressure measurement, and in particular to an oscillometric-based method for intermittent measurement and a volume-clamp-based method for continuous measurement.

BACKGROUND

Capillaries are microvessels that allow for the exchange of substances between blood and tissue, which is the primary purpose of the cardiovascular system. Capillary blood pressure is a major force for the capillary exchange. Persistently high capillary blood pressure can damage the vulnerable capillary wall and cause capillary leakage and edema formation. When the capillary pressure is too low, the surrounding tissue can be under-nourished and may result in ischemic ulcers. For congestive heart failure with blood backing up in the veins and capillaries, the elevated capillary blood pressure can result in peripheral edema and enlarged organs. Therefore, capillary blood pressure provides significant diagnostic and prognostic value for ulceration and heart failure.

Clinically adopted tools for microcirculation assessment include laser doppler flowmetry (LDF), transcutaneous oximetry, and capillaroscopy which look into the flow profile, oxygen supply, and morphology changes of the capillaries. These tools are expensive and require well-trained clinical professionals to operate these tools and cannot be used by patients themselves at home. More importantly, these tools are unable to probe the capillary blood pressure, which has a direct impact on the capillary exchange. Current blood pressure devices measure the blood pressure in arteries and mainly indicate the circulation condition in macrocirculation. The existing technique for measuring capillary blood pressure is invasive and requires a micropipette to be inserted into the nail fold capillary and a sophisticated servo-nulling micropressure measuring system.

BRIEF SUMMARY

Embodiments of the subject invention provide devices and methods for non-invasive capillary blood pressure measurement. Other embodiments of the subject invention provide air pressure control strategies for improving the signal-to-noise ratio of the signals that indicate the capillary pulsations.

The devices and methods extend the established oscillometric and volume-clamp methods for arterial blood pressure measurement to capillary blood pressure measurements at body sites having a sufficient capillary density. An device can comprise: a front end in contact with the body to compress and decompress the capillaries in the tissue, a pressure control module for regulating the contact pressure between the front end and the tissue, a pressure transducer coupled to the front end for measuring the contact pressure or the pressure exerted on the capillaries, a capillary sensing module for detecting the capillaries' pulsations under the contact pressure modulation, and an algorithm for determining the capillaries' pressure from the traces of capillary pulsation signals and the contact pressure signal.

During the oscillometric capillary blood pressure measurement, the contact pressure can first be increased linearly above the capillary blood pressure and then decreased linearly to zero via a pressure control module. A capillary sensing module containing one or more optical/piezoelectric/ultrasonic/imaging sensors is used to obtain capillary pulsation signals. When the contact pressure is equal to the capillary blood pressure in certain segments of the capillaries, the capillary wall exhibits its greatest compliance. Thus the capillary pulsation signal detected by the capillary sensing module will present its local maximum in the oscillation amplitude during an increase or decrease of the contact pressure. The contact pressure values corresponding to the peaks of the capillary oscillation signal are taken as the mean blood pressure in the capillaries of the measurement site. Particularly, the disclosed oscillometric method for measuring capillary blood pressure can be integrated with a conventional arterial blood pressure device for simultaneous measurement of both arterial and capillary blood pressure.

In a volume-clamp method for continuous capillary blood pressure measurement, the capillary sensing module can comprise a photoplethysmography sensor of which the incident light includes at least one wavelength component that only travels within the superficial capillary layer of the skin before arriving at a light detector. The pressure control module is a servo-nulling system which regulates the contact pressure to balance with the capillary pressure inside the tissue by keeping the capillary volume pulse detected by the capillary sensing module constant. The variation trace of the contact pressure is then regarded as the capillary blood pressure.

To improve the signal-to-noise ratio and the measurement efficiency of the system, embodiments of the subject invention can also include an inflatable cuff-based front end. The front end can also comprise multiple inflatable cuff units. Each inflatable cuff unit can be a small cuff with one capillary pulsation sensor unit or a large cuff with multiple capillary pulsation sensor units. The setup allows for a larger volume of air flow through the pressure control components, e.g., air pump and air valve, thus minimizing the perturbation from the active pressure regulation induced pressure fluctuation. An additional air storage unit can be introduced into the pressure control module to increase the total compressed air volume, thus avoiding an oversized front end. Meanwhile, the connection of multiple front-end units placed at various body sites allows for simultaneous measurement of capillary blood pressure at multiple body sites via the oscillometric method.

DETAILED DISCLOSURE

The methods and devices of the subject invention provide accurate capillary blood pressure measurements for mobile health applications. The devices can take measurements from a subject, display the results automatically, and are suitable for general clinical use and home use.

Figure 1:
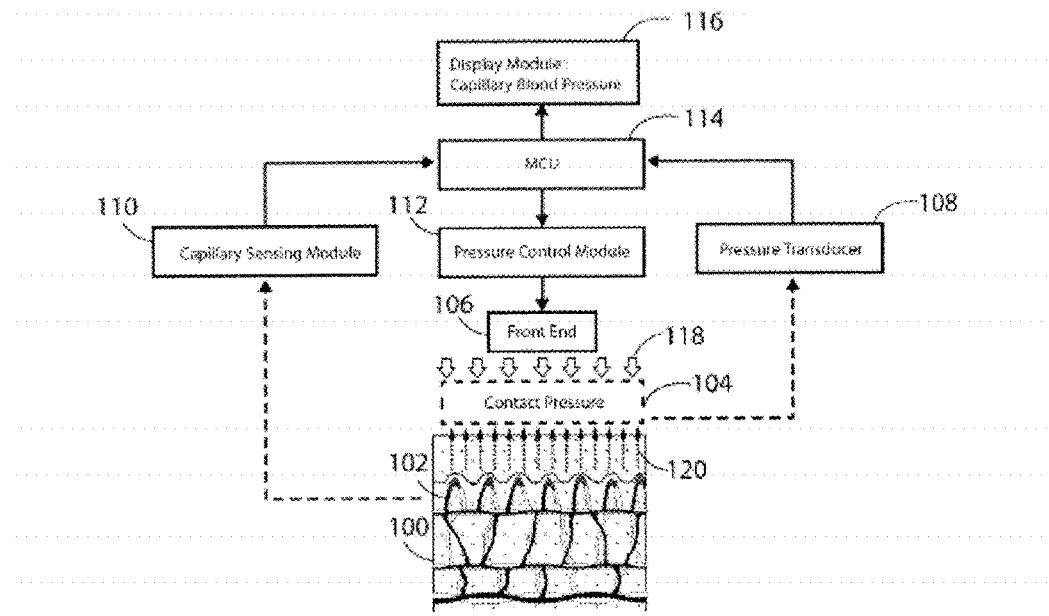
FIG. 1 shows the schematic structure of a non-invasive capillary blood pressure monitor.

As seen in FIG. 1, a non-invasive capillary blood pressure measuring device can comprise a front end 106 in contact with skin 100 and configured to exert compression pressure 118 against the skin and the capillaries 102 lying in the superficial layer of the skin, a pressure transducer 108 measuring the contact pressure 104, a capillary sensing module 110 for detecting the capillary pulsation, a pressure control module 112 coupled to the front end 106 to change the compression pressure 118, a microcontroller unit (MCU) 114, and a display module 116 configured to show the capillary blood pressure values and other complimentary physiological parameters to a user.

The MCU 114 can be configured to receive signals generated by the capillary sensing module 110 and the pressure transducer 108, utilize the compression pressure control scheme to give control signals to the pressure control module 112, and determine the capillary blood pressure values using a pre-defined algorithm. The contact pressure can be simultaneously modulated by the active compression pressure 118 and the capillary pressure pulsation 120 transmitted to the skin surface.

In one embodiment, the front end 106 is an inflatable cuff which can be wound around a body part. The pressure transducer 108 is an air pressure sensor coupled to the front end 106 to measure the air pressure in the inflatable cuff. The pressure control module 112 is also connected to the front end 106 to inflate and deflate the cuff.

In another embodiment, the front end 106 is a compression plate that is held against the skin's surface. The pressure transducer 108 is placed on the surface of the plate in contact with the skin 100 to measure the contact pressure 104. The pressure control module 112 can be a mini-motor to propel the compression plate towards the skin 100 in order to apply a varying amount of extrusion force.

The function of the capillary sensing module 110 is to detect the capillary pulsation. It can comprise one or a combination of the sensors including an optical, a piezo-electrical, an ultrasonic, or an imaging sensor. One preferred sensor is a photoplethysmography (PPG) sensor, for example a pulse oximeter, which uses incident light at an appropriate wavelength. For measuring the capillary 102 pulsations in the superficial layer of the skin, the suggested light wavelength for the PPG sensor is in the vicinity of 450 nm to 570 nm. For an ultrasonic sensor, the frequency of the ultrasound should be adjusted to only penetrate to the capillaries in the skin and not reach the arteries in the deeper skin layers. The suggested frequency of the ultrasound is around 2 MHz, of which the estimated penetration depth is approximately 1.5 mm. An imaging sensor, for example, a videocapillaroscopy sensor, for recording the real-time morphology changes of the capillary loops and registering the occlusion level of the capillary, can also serve as the capillary sensing module 110. When the contact pressure is in the range of the capillary blood pressure, the AC component of a piezoresistive sensor, an air pressure sensor connected to the cuff, or a strain gauge in direct contact with the body can also indicate the capillary pulsation.

The MCU 114 can be configured to execute one or both of the oscillometric method and volume-clamp method and the corresponding pressure control algorithms. The display module 116 is the user interface for displaying the measured capillary blood pressure values. In one embodiment, the display module is a screen integrated into the measurement device. In some embodiments, the display module can also be the main panel of a sophisticated multi-functional physiological measurement system, or smart mobile device comprising a phone, watch, or tablet.

Figure 2:
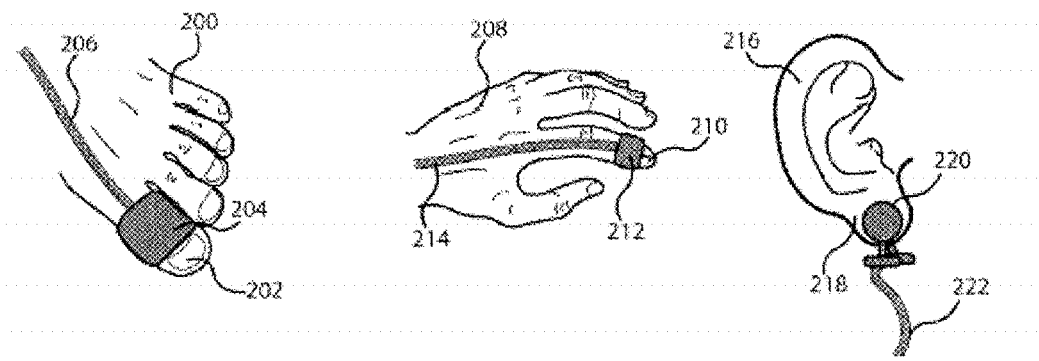
FIG. 2 shows the front end worn on various body sites for capillary blood pressure measurement.

In an embodiment, the front end 106 is placed at a location on the body with a relatively higher capillary density (for example, fingertips, toes, or earlobes). FIG. 2 illustrates front ends 204, 212, and 220 placed at the great toe 202 of the foot 200, the tip of the index finger 210 of hand 208, and the earlobe 218 of the ear 216.

In another embodiment, the front ends 204 and 212 are inflatable air cuffs and the communication lines 206 and 214 are integrated air tubes and the signal lines. The front end 220 has a clip-like structure for clipping on the earlobe 218. In another embodiment, the distance between the two plates on earlobe front end 220 is fixed. There can be an inflatable airbag on at least one side of the earlobe front end 220. Then by inflating or deflating the cuff, the contact pressure between the front end 220 and the earlobe 218 is increased or decreased, respectively. The communication line 222 can be an integrated air tube and a signal line. In yet another embodiment, the two plates of the front end 220 are not fixed. The contact pressure is varied by adjusting the opening degree of the two plates and the communication line 222 is just a signal line.

Figure 3A:
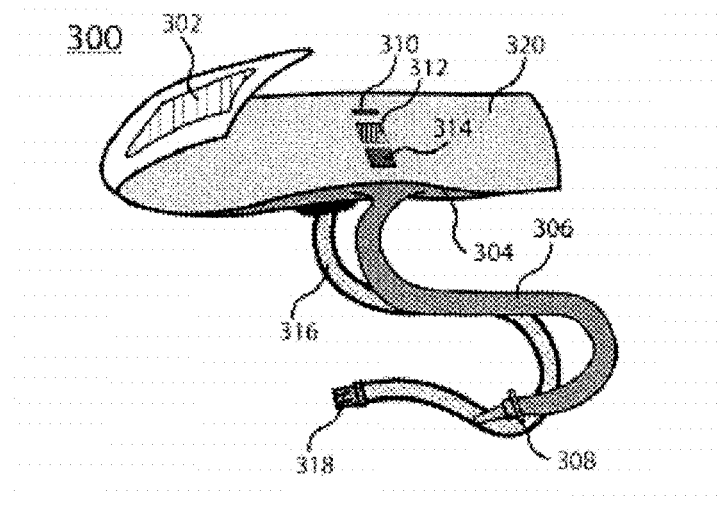
FIG. 3a shows an inflatable mini-cuff based version of the front end and pressure control module.

As seen in FIG. 3a, the front end 300 can be a mini-cuff to be worn on a fingertip or toe. The mini-cuff can be wrapped around a measurement site firmly with the aid of the fastening tape 302. The cuff-based front end can minimize the size of the front end to provide better user comfort. The inflatable air bladder 304 is put inside a fabric cover 320. One end of the air tube 306 is connected to the air bladder 304, and the other end is connected to a connector 308 which can be connected to the pressure control module 360. The signal line 316 with the signal interface 318 streams out the capillary pulsation signals generated by the capillary sensing module. In certain embodiments, the capillary sensing module is embedded in the sensor. In other embodiments, the capillary sensing module is composed of a PPG sensor comprising a blue light emitter 310 and a light detector 314 or a piezoelectric sensor 314. The light emitter includes comprises a light emitting diode and a laser diode. The light detector comprises a photodiode and a phototransistor. The pressure sensor 314 comprises a piezoresistive or a piezocapacitive pressure sensor. Incorporating a multi-modality capillary pulsation sensor can provide more information, thus providing more accurate capillary blood pressure measurements.

Figure 3B:
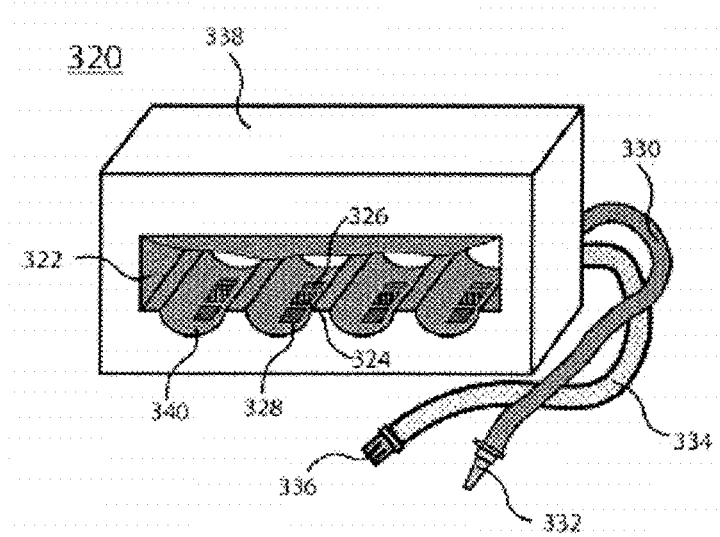
FIG. 3b shows a measuring box based version of the front end and pressure control module.

One possible drawback of the single mini-cuff in the front end is the low signal-to-noise ratio due to the pressure fluctuations caused by the active pressure control during cuff inflation/deflation and small air volume of air. In general, a large cuff with linear pressure increase/decrease rate yields precision measurement. As seen in FIG. 3b, the front end comprises at least one measuring box 320. The measuring box 320 has a rigid housing 338. Inside the measuring box 320, there is a relatively large air bladder 322 sealed in the rigid housing 338. The air bladder 322 is connected to an air tube 330 that is connected to the pressure control module 360 via the air connector 332. There are grooves 340 inside the measuring box 320 for putting fingers or toes. Each groove 340 has independent embedded capillary sensing units for measuring the capillary pulsation of the body part resting on the groove. In one further embodiment, each capillary sensing units comprises a blue PPG sensor including a blue LED 326, a light detector 328, and a pressure sensor 324 lying between the blue LED 326 and the light detector 328. This set up provides better signal-to-noise ratio by increasing the volume of the air bladder and higher efficiency by simultaneously taking the capillary blood pressure measurements of multiple body parts.

Figure 3C:
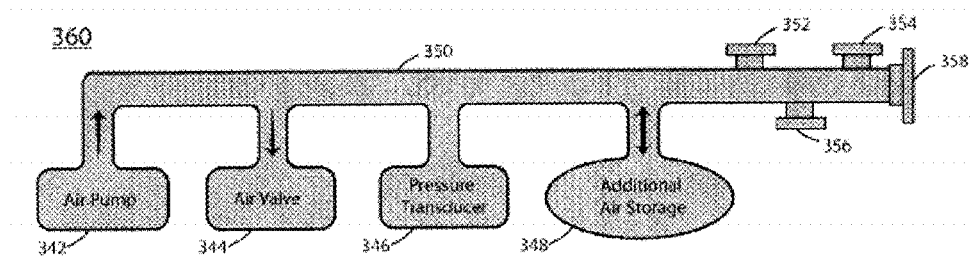
FIG. 3c shows an air pressure manipulation module version of the front end and pressure control module.

FIG. 3c illustrates an air pressure manipulation module 360. The air pressure manipulation module 360 utilizes an air pump 342 and an air valve 344 for cuff inflation and deflation respectively. The air pump 342 and the air valve 344 are connected via the main air path 350. The main air path 350 also provides a path for air to flow to the cuffs in the front ends. An air pressure transducer 346 is also connected to the main air path 350 for detecting the pressure within the control air volume.

In certain embodiments, the outputs from the air pressure transducer 346 are fed into the MCU of the capillary pressure monitor to actively regulate the cuff pressure. To minimize the control noise of the closed-loop control, the amount of the control air volume can be increased. In some embodiments, the front end contains multiple cuffs which can be all connected to the main path to additional air connectors 352, 354, and 356. In some embodiments, the air pressure manipulation module 340 has an additional air storage component 348. For example, the additional air storage component 348 can be a flexible balloon. The additional air storage component 348 can be designed for material compliance and the maximum inflation volume. In another embodiment, the additional air storage component 348 is a larger cuff placed at other body sites comprising arms, wrists, legs and/or ankles for measuring arterial blood pressure or multiple connected cuffs at peripheral body sites like the fingertips and toes allowing for simultaneously measurement of the capillary blood pressure values.

In one embodiment, the device comprises a photoplethysmography sensor, a laser Doppler sensor, and an ultrasound sensor, wherein a physical set-up of the device is optimized by using at least one of the following parameters: (1) a distance between each sensor and a receiving unit, (2) a wavelength of an emitted wave from a transmitting unit, (3) a frequency of an emitted wave from the transmitting unit, and (4) an intensity of an emitted wave from the transmitting unit.

The device can emit light from an optical emitter of the photoplethysmography sensor and the laser doppler sensor at a wavelength in or near a range of 450 nm to 570 nm. The emitted ultrasound frequency of the ultrasound sensor can be approximately 2 MHz.

The pressure control module can comprises a close-loop pressure control unit that actively controls the contact pressure based on contact pressure values provided by the pressure transducer. The pressure control module can comprise at least one air pump in operable communication with the inflatable cuff and at least one air valve in operable communication with the inflatable cuff.

A complementary air storage unit can be a larger cuff placed at other sites of the subject comprising arms, wrists, legs, or ankles for measuring arterial blood pressure or multiple connected cuffs at peripheral sites of the subject, comprising fingertips or toes that allow for simultaneously measurement of capillary blood pressure values at the peripheral sites.

Figure 4A:
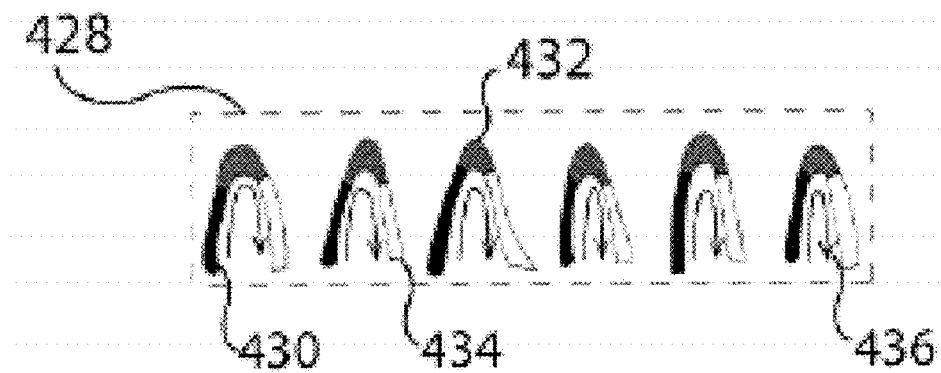
FIG. 4a shows a diagram of the capillaries of a subject in need of treatment.
Figure 4B:
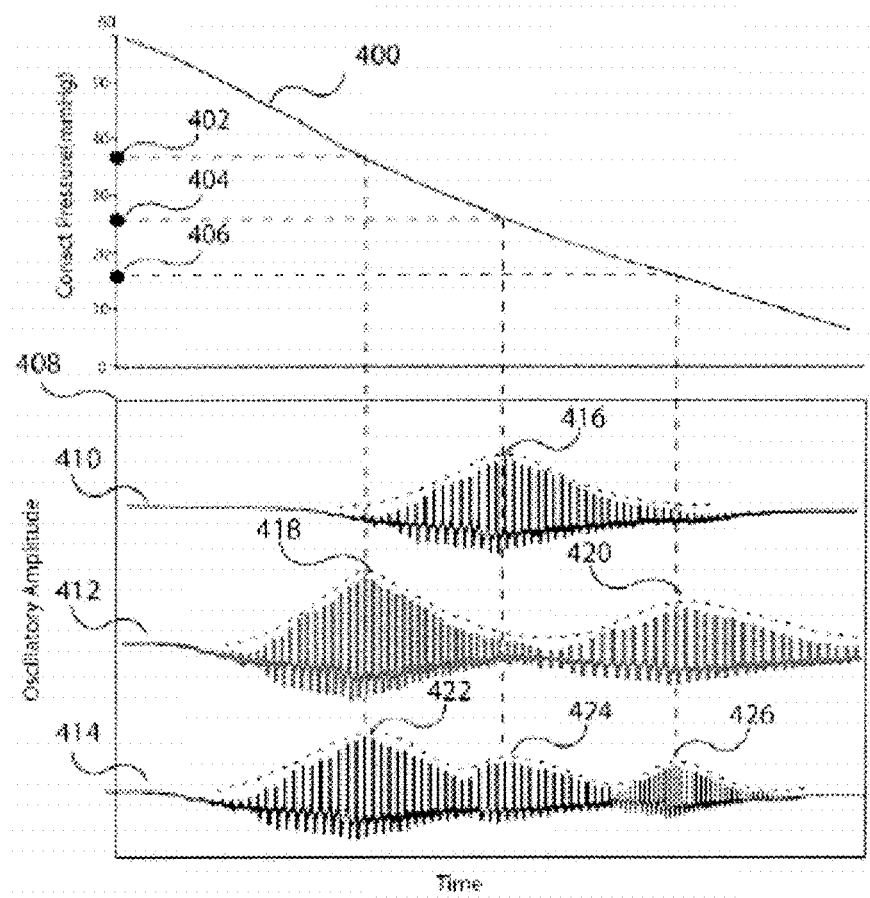
FIG. 4b shows a diagram comparing the contact pressure decreasing curve and the capillary oscillometric signals.

FIGS. 4a and 4b illustrate an oscillometric based method for measuring capillary blood pressure. The basic working principle of the oscillometric method is that the pulse vibration of a blood vessel segment reaches a maximum in the oscillation amplitude when contact pressure exerted on the blood vessel segment is nearly equal to the mean blood pressure in the compressed blood vessel segment. Systolic and diastolic pressures can be estimated as the contact pressure points corresponding to certain ratios of the peak oscillation amplitudes for the mean blood pressure in the vibration distribution.

Therefore, by observing the oscillation amplitudes of the detected capillary pulse during the increase/decrease of contact pressure applied to a capillary bed, the mean/systolic/diastolic capillary blood pressure values can be determined. In certain embodiments, the measurement sites are kept at the same sagittal plane as the heart. In other embodiments, the detected results are standardized by removing the hydrostatic effect caused by the height difference between the measured location and the heart.

As seen in FIG. 4a, the end-capillaries 428 in the skin are composed of an arteriolar limb 430, and a venous limb 434 joined in a capillary dome to form a loop oriented more or less perpendicularly to the skin surface. The capillary blood flow direction 436 is from the arteriolar limb 430 to the venous limb 434. Therefore, the capillary blood pressure decreases from the arteriolar end 430, the capillary apex 432 to the venous end 434. The normal values of capillary blood pressure are about 35 mmHg in the arteriolar limb 430 and 15 mmHg in the venous limb 434. The blood pressure pulsation amplitude in capillaries 428 is at a magnitude of 10 mmHg, which is lower than the pressure in the arteries. Therefore, the morphology of the oscillation envelope is dependent on the sensitivity of the capillary sensing module. Accordingly, the capillary blood pressure values for specific capillary segments can be determined.

In FIG. 4b, the contact pressure decreasing curve 400 and the capillary oscillometric signals 408 are compared. The contact pressure decreasing curve shows a linear decrease in pressure from the diastolic arterial blood pressure to zero at a rate of approximately 2 mmHg/s. In one embodiment, the amplitude envelope of the detected capillary oscillometric signal 410 has one peak 416, corresponding to a contact pressure 404, which is taken as the mean capillary blood pressure at the capillary apex 432. In another embodiment, the amplitude envelope of the detected capillary oscillometric signal 412 has two peaks 418 and 420 corresponding to the contact pressure 402 and 406, which are taken as the mean capillary blood pressure at the arteriolar limb 430 and the venous limb 434. In yet another embodiment, the amplitude envelope of the detected capillary oscillometric signal 414 has three peaks 422, 424, and 426, corresponding to the contact pressure 402, 404, and 406, which are taken as the mean capillary blood pressure at the arteriolar limb 430, the apex 432, and the venous limb 434.

In even other embodiments, the systolic and diastolic capillary blood pressure can be calculated from the relative oscillation amplitude ratio to the corresponding mean capillary blood pressure peak.

The oscillometric capillary blood pressure measurement can be integrated with the oscillometric arterial blood pressure measurement. The system allows for simultaneous arterial and capillary blood pressure measurement with one cuff inflation and deflation procedure.

Figure 5A:
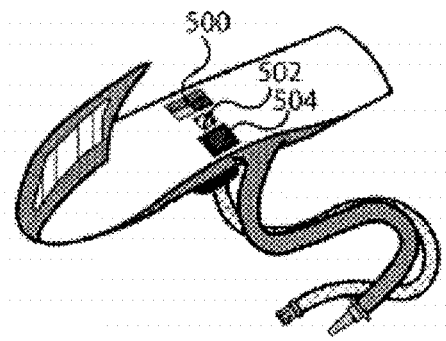
FIG. 5a shows an inflatable mini-cuff based version of the front end and pressure control module.

As seen in FIG. 5a, the front end is a mini-cuff that can be wound on one fingertip. The capillary sensing module comprises multi-wavelength LEDs 500, a photodiode 504, and a pressure sensor 502.

Figure 5B:
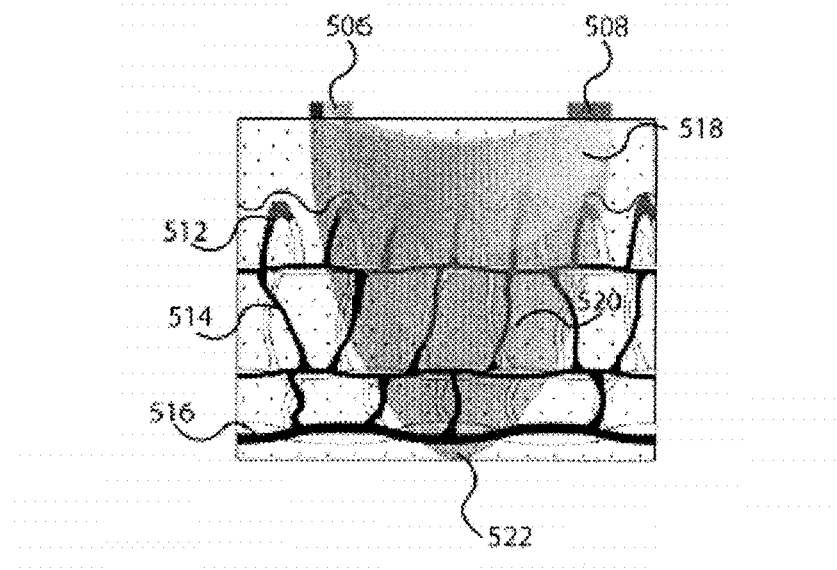
FIG. 5b shows a diagram of multi-wavelength LEDs emitting blue light, yellow light, and infrared (IR) light into the skin.
Figure 5C:
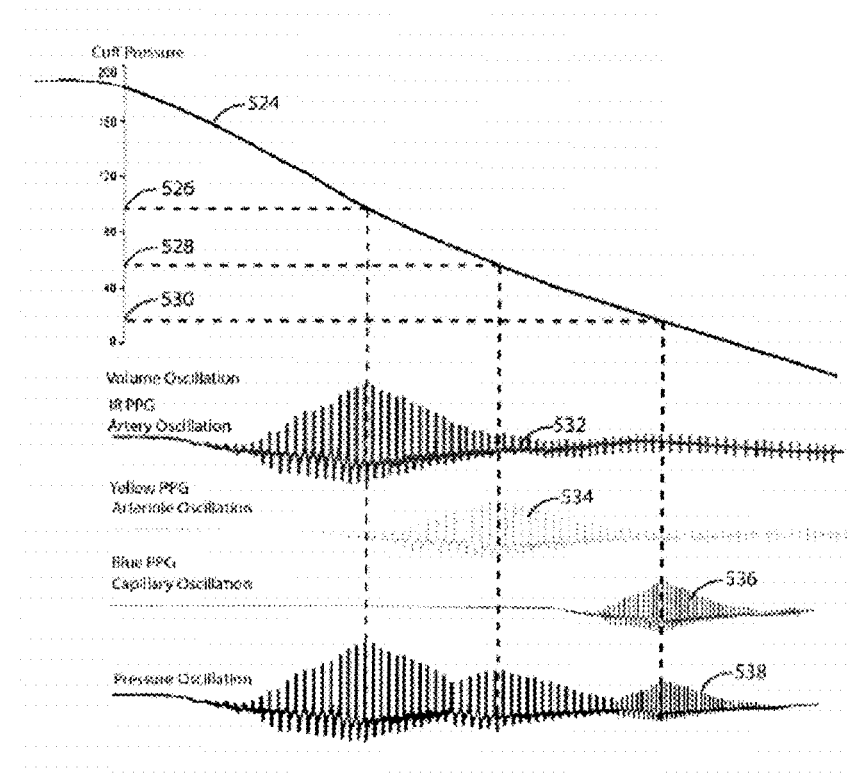
FIG. 5c shows a plot of cuff pressure integrated with an associated infrared photoplethysmography (IR PPG) artery oscillation signal, a yellow PPG arteriole oscillation signal, a blue PPG capillary oscillation signal, and a pressure oscillation signal.

As illustrated in FIG. 5b, the multi-wavelength LEDs 506 can emit blue light 518, yellow light 520, and infrared (IR) light 522 into the skin. The photodetector detects the multi-wavelength light coming out from the skin. In one embodiment, the multi-wavelength sensor comprises multi-wavelength LEDs 506 and one photodetector 508 working in a time-multiplexing mode, so that multi-wavelength PPG signals are collected simultaneously. The light can travels through different layers of the skin and therefore the multi-wavelength PPG signal can contain different physiological information. Blue PPG mainly reflects capillary pulsation since blue light 518 can only reach the superficial skin capillaries 512. Yellow PPG further contains arteriole pulsation information since the yellow light 520 goes deeper into the communicating arterioles 514 in the dermis. Red PPG also contains the artery pulsation due to the penetration ability of IR light 522 into the arteries 516 in the subcutaneous layer. In one embodiment, as seen in FIG. 5c, the raw infrared (IR) PPG signal and yellow PPG signal are adopted as the artery oscillation 532 and arteriole oscillation 534, respectively.

In another embodiment, the artery oscillation signal 532 and arteriole oscillation signal 534 are reconstructed from the multi-wavelength PPG signals to remove any unwanted oscillation component. For example, to derive a pure arteriole pulsation or capillary pulsation the blue PPG can be removed from yellow PPG which is a mixture of capillary and arteriole pulsation. When applying the oscillometric method for both arterial systolic blood pressure and capillary blood pressure measurement the cuff pressure can be decreased linearly at a rate of 0.5-3 mmHg/s from a cuff pressure point larger than the arterial blood pressure as depicted by the cuff pressure curve 524.

In some embodiments, the IR PPG signal, yellow signal, and blue PPG signal are recorded during the cuff deflation. The oscillometric signals detected or derived from the multi-wavelength PPG sensor are treated as the volume oscillometric signals of the blood vessels. The volume oscillation signals at least include artery oscillation 532, arteriole oscillation 534 and capillary oscillation 536. The contact pressure values corresponding to the peaks of the artery oscillation 532, arteriole oscillation 534 and capillary oscillation 536 are registered as the mean arterial blood pressure 526, the mean arteriolar blood pressure 528, and the mean capillary blood pressure 530, respectively.

The oscillometric signal detected by the pressure sensor can also be recorded. The pressure oscillation 538 is extracted from the air pressure sensor connected to the front end, which is an inflatable cuff. In another embodiment, the pressure oscillation 538 is registered by a pressure sensor integrated into a front end in contact with the body. The pressure oscillation pressure signal 538 is supposed to have at least three peaks during the pressure decay from a pressure higher than the arterial blood pressure. The contact pressure values corresponding to the peaks of the pressure oscillation 538 envelop from larger to small are taken as the mean arterial blood pressure 526, the mean arteriolar blood pressure 528 and the mean capillary blood pressure 530 respectively.

In an embodiment, the oscillometric method comprises adjusting the contact pressure with the pressure control unit between a pressure value under a lowest value of the capillary blood pressure and a pressure value above a highest value of the capillary blood pressure. A next step can be to calculate capillary pulsation envelopes from capillary oscillometric signals extracted as a heartbeat-synchronous AC component of an output of the capillary sensing module. A next step can be to identify the contact pressure values corresponding to an occurrence of peaks in the capillary pulsation envelopes. A next step can be to determine the MBP of different capillary sites based upon a morphology of the capillary pulsation envelopes. Afterwards, the SBP and DBP values of different capillary sites can be determined as the contact pressure value corresponding to oscillation amplitudes of certain predefined amplitude ratios to peak oscillation amplitudes for the MBP value in the capillary oscillometric signal.

In the volume-clamp method, the blood volume in the tissue is measured by the light sensor, for example, a PPG sensor. The contact pressure varies to match the blood pressure inside the blood vessels probed by the light so that the resulting light signal is kept constant. As blood volume and, thus, the light signal is held constant over time, the intra-arterial pressure is equal to the varying contact pressure. This volume-clamp method can measure arterial blood pressure with the aid of an IR PPG sensor indicating the blood volume of arteries.

The volume-clamp method can also comprise an initial step of adjusting the contact pressure to adjust a signal to noise ratio of a capillary volume pulsation signal. A next step can be to modulate the contact pressure to keep the capillary volume pulsation signal constant. A next step can be to generate the capillary pressure waveform from a modulated contact pressure trace.

Embodiments of the subject invention extend the volume-clamp method for measuring continuous capillary blood pressure by using light with a shorter wavelength to only measure the skin capillary blood volume. The continuous capillary blood pressure waveform is derived from the contact pressure variation trace which is keeping the capillary volume signal constant. The measurement sites can be maintained at the same sagittal plane as the heart. In some embodiments, the detected results are standardized by removing the hydrostatic effect caused by the height difference between the measuring site and the heart.

Figure 6:
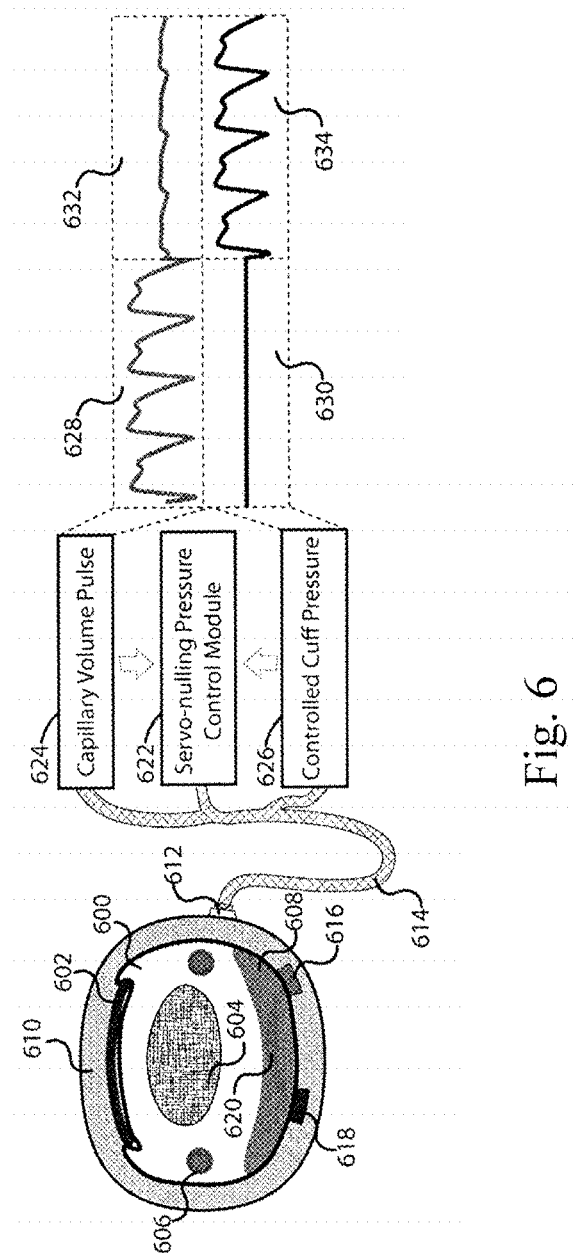
FIG. 6 shows a schematic diagram for continuous capillary blood pressure measurement based on a volume clamp method.

FIG. 6 depicts the continuous capillary blood pressure measurement at a fingertip 600 with a finger cuff 610. The fingertip 600 contains a nail 602, a bone 604, and digit arteries 606 at the sides of the finger and the capillary bed 608 in the finger pulp. In certain embodiments, a blue PPG sensor comprising a blue LED 616 and a photodiode 618 is used for monitoring capillary blood volume as blue light 620 has a short penetration depth into the skin and can only travel into the capillary bed 608. The finger cuff 610 is wrapped around the fingertip 600, exerting the contact pressure to the capillary bed 608. Connector 612 attached to the finger cuff 610 is connected to the composite communicating line 614 for signal transmission and air pathway. The composite communicating line 614 keeps streaming the signal of the capillary volume pulse 624 and the controlled cuff pressure 626. The capillary volume pulse 624 and the controlled cuff pressure 626 are fed into the servo-nulling pressure control module 622. During the measurement in the initialization phase, at least one level of constant cuff pressure 630 is applied, and capillary pulsation 628 of good signal quality is recorded. In the measuring phase the servo-nulling pressure control module 622 then actively regulates the cuff measure 634 to match the inside pressure pulsation in the capillary bed 608 to make the capillary pulsation 632 fully suppressed to keep a constant capillary blood volume.

The minor pulsation in the capillary pulsation signal 632 can be set to make sure that the cuff pressure is not so high as to occlude the capillaries. Then the corresponding cuff pressure trace 634 is taken as the capillary blood pressure waveform.

In an embodiment, the measured capillaries blood pressures values to be measured comprise one of the following: (1) systolic blood pressure (SBP) value, mean blood pressure (MBP) value, or diastolic blood pressure (DBP) value of an arteriole end of capillaries, (2) an SBP, an MBP, or a DBP value of an apex of the capillaries, and (3) an SBP, an MBP, or a DBP value of a venous end of the capillaries.

Simultaneous oscillometric arterial and capillary blood pressure measurement can be achieved by increasing contact pressure between the front end and the measuring site to a value higher than a value of the arterial systolic blood pressure and decreasing the contact pressure to zero. A next step can be to simultaneously record a contact pressure changing curve and receive arterial, arteriolar, and capillary oscillometric signals from capillary sensing module. A next step can be to determine arterial, arteriolar and capillary blood pressure values from the contact pressure curve and the pulsation envelopes derived from the arterial and arteriolar, capillary oscillometric signals. The arterial, arteriolar and capillary oscillometric signals can be derived from multi-wavelength photoplethysmography sensors or the contact pressure signal obtained under different ranges of contact pressure. The contact pressure can be increased and/or decreased linearly at an average rate between 0.5-3.0 mm Hg/second. Noise induced by the close-loop pressure control to the capillary pulsation signal can be reduced by adding a complementary air storage unit in operable communication with the inflatable cuff or adjusting the compliance of the inflatable cuff.

The methods and processes described herein can be embodied as code and/or data. The software code and data described herein can be stored on one or more (non-transitory) machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A non-invasive peripheral capillary blood hydrostatic pressure measuring device, comprising:
    a front end configured to be wrapped around a measuring site and to exert external pressure on the measuring site, wherein the measuring site is at least one of a finger of a subject and a toe of the subject, wherein a surface tissue of the measuring site is perfused with capillaries, and wherein the surface tissue is of skin of the subject;
    a pressure transducer coupled to the front end that detects the contact pressure exerted on the measuring site by the front end;
    a pressure control module that modulates the contact pressure between the front end and the surface tissue;
    a capillary sensing module that measures capillary blood pulsation signals at the measuring site, wherein the capillary blood pulsation signals reflect at least one of capillary blood volume and capillary wall motion of the capillaries in the surface tissue;
    a non-transitory computer readable medium comprising stored instructions that when executed cause at least one processor to determine capillary blood hydrostatic pressure values based upon the received capillary blood pulsation signals measured by the capillary sensing module and the contact pressure detected by the pressure transducer;
    a microcontroller; and
    a display module that displays the capillary blood hydrostatic pressure values,
    wherein the front end comprises an inflatable cuff configured to cover the measuring site and configured to be removed after use,
    wherein the inflatable cuff comprises an outer surface and an inner surface, wherein the outer surface of the inflatable cuff is rigid, thereby limiting an air volume in the inflatable cuff, wherein the inner surface faces the measuring site during use and is flexible and conforms to the surface tissue, and
    wherein the pressure transducer is an air pressure sensor connected to the inflatable cuff or a piezoelectric sensor configured to be disposed between the inflatable cuff and the measuring site.

2. The device of claim 1, wherein the capillary sensing module comprises at least one of a photoplethysmography sensor, a laser doppler sensor, an ultrasound sensor, a pressure sensor configured to operate under a predetermined contact pressure regime, or an imaging sensor configured to monitor morphology changes of the capillaries.

3. The device of claim 2, wherein the capillary sensor module comprises a photoplethysmography sensor, a laser doppler sensor, and an ultrasound sensor.

4. The device of claim 3, wherein a wavelength of light emitted from a respective optical emitter of each of the photoplethysmography sensor and the laser doppler sensor is in a range of 450 nm to 570 nm, and wherein an emitted ultrasound frequency of the ultrasound sensor is 2 MHz.

5. The device of claim 3, wherein the capillary hydrostatic blood pressure values are determined based on an oscillometric method for intermittent measurement, and
wherein the capillary hydrostatic blood pressure values are further determined from a continuous morphology change of capillary pulsations during changes of the contact pressure between the front end and the surface tissue.

6. The device of claim 5, wherein the capillary blood hydrostatic pressure values to be measured include at least one of the following parameters:
systolic blood pressure (SBP), mean blood pressure (MBP), or diastolic blood pressure (DBP) of an arteriole end of the capillaries;
SBP, MBP, or DBP values of an apex of the capillaries; and
SBP, MBP, or DBP values of a venous end of the capillaries.

7. The device of claim 5, wherein the oscillometric method comprises:
varying the contact pressure monotonically at an average rate between 0.5-3.0 mm Hg/second with the pressure control module between a pressure value under a lowest value of the capillary blood pressure values and a pressure value above a highest value of the capillary blood hydrostatic pressure values;
calculating capillary pulsation envelopes from capillary oscillometric signals extracted as a heartbeat-synchronous alternating current (AC) component of an output of the capillary sensing module;
identifying contact pressure values corresponding to an occurrence of peaks in the capillary pulsation envelopes;
determining respective MBP values for different capillary sites based upon a morphology of the capillary pulsation envelopes; and
determining respective SBP and DBP values for different capillary sites as a contact pressure value corresponding to oscillation amplitudes of certain predefined amplitude ratios to peak oscillation amplitudes for the MBP values in the capillary oscillometric signals.

8. The device of claim 7, wherein determining the MBP values for different capillary sites further comprises one of the following:
a) if there are three peaks in the pulsation envelopes of the oscillometric signals, the contact pressure values from large to small are MBP values of an arteriolar end, an apex, and a venous end of the capillaries; or
b) if there are two peaks in the pulsation envelopes of the oscillometric signals, corresponding contact pressure values from large to small are MBP values of an arteriolar end and a venous end of the capillaries; or
c) if there is only one peak in the pulsation envelopes of the oscillometric signals, a corresponding contact pressure value is a MBP value of an apex of the capillaries.

9. The device of claim 1, wherein the capillary blood hydrostatic pressure values are further determined based on a volume-clamp method for continuous measurement, and
wherein the capillary blood hydrostatic pressure values are further determined based on variations in the contact pressure between the front end and the surface tissue, which maintains a blood volume of a capillary at the measuring site constant.

10. The device of claim 9, wherein the volume-clamp method comprises:
adjusting the contact pressure to adjust a signal-to-noise ratio of a capillary volume pulsation signal;
modulating the contact pressure continuously and actively with the pressure control module to keep the capillary volume pulsation signal constant; and
generating a capillary pressure waveform from a modulated contact pressure trace.

11. The device of claim 1, wherein the measuring site is horizontal to a heart of the subject, and wherein the instructions when executed further cause the at least one processor to standardize received signal values in order to remove any hydrostatic effect that is created due to a height difference between the measuring site and the heart of the subject.

12. The device of claim 1, wherein the pressure control module is configured to actively control the contact pressure based on contact pressure values provided by the pressure transducer.

13. A method for simultaneous oscillometric arterial and capillary blood hydrostatic pressure measurement, comprising:
providing a non-invasive capillary blood hydrostatic pressure measuring device as described in claim 12;
increasing the contact pressure between the front end and the capillaries at the measuring site to a value higher than a value of arterial systolic blood pressure and decreasing the contact pressure to zero;
simultaneously recording a contact pressure curve and oscillometric signals of an arterial pulsation, arteriolar pulsation, and capillary oscillometric signals; and
determining arterial, arteriolar, and capillary blood hydrostatic pressure values from the contact pressure curve and pulsation envelopes derived from the arterial, arteriolar, and capillary oscillometric signals.

14. The method of claim 13, wherein the arterial, arteriolar, and capillary oscillometric signals are derived from multi-wavelength photoplethysmography sensors or a contact pressure signal obtained under different ranges of contact pressure.

15. The method of claim 13, wherein the contact pressure is adjusted linearly at an average rate between 0.5-3.0 mm Hg/second.

16. The method of claim 13, further comprising reducing noise induced to the capillary blood pulsation signals by:
adding a complementary air storage unit configured to be in operable communication of flow with the inflatable cuff; or
adjusting a compliance of the inflatable cuff.

17. The method of claim 16, wherein the complementary air storage unit is:
a larger cuff placed at alternate sites of the subject comprising arms, wrists, legs, or ankles for measuring arterial blood pressure; or
multiple connected cuffs at peripheral sites of the subject, the peripheral sites comprising fingertips or toes, that allow for simultaneous measurement of capillary blood hydrostatic pressure values of the peripheral sites.

18. The device of claim 1, wherein the pressure control module further comprises:
- at least one air pump configured to be in operable communication with the inflatable cuff; and
- at least one air valve configured to be in operable communication with the inflatable cuff.

\* \* \* \* \*